United States Patent [19]

Keller

[11] Patent Number: 4,957,743

[45] Date of Patent: Sep. 18, 1990

[54] METHOD FOR TREATING HERPES

[76] Inventor: Helmut Keller, Blumenstrasse 032, D-8646 Nordhalben, Fed. Rep. of Germany

[21] Appl. No.: 892,226

[22] Filed: Jul. 31, 1986

[30] Foreign Application Priority Data

Jul. 31, 1985 [EP] European Pat. Off. ......... 85109616.4
Jul. 31, 1985 [EP] European Pat. Off. ......... 85109617.2

[51] Int. Cl.$^5$ .............................................. A61K 35/78
[52] U.S. Cl. ................................... 424/195.1; 514/934
[58] Field of Search ...................... 424/195.1; 514/934

[56] References Cited

FOREIGN PATENT DOCUMENTS 0019808 12/1980 European Pat. Off. ......... 424/195.1

OTHER PUBLICATIONS

EHK Acta Medica Empirica, Bd. 34, 416–420, 1985.

Primary Examiner—John W. Rollins
Attorney, Agent, or Firm—Klein & Vibber

[57] ABSTRACT

This application relates to a composition and method for treating herpes and chronic inflammatory intestinal tract diseases. According to the invention, herpes, Morbus Crohn and Colitis ulcerosa are treated with a medication prepared from the juice or watery extract of meat-eating plants, preferably the Venus Fly Trap (*Dionaea muscipula*).

4 Claims, No Drawings

METHOD FOR TREATING HERPES

This application relates to a composition and method for treating herpes and chronic inflammatory intestinal tract diseases. According to the invention, herpes, Morbus Crohn and Colitis ulcerosa are treated with a medication prepared from the juice or aqueous extract of meat-eating plants, preferably the Venus Fly Trap (*Dionaea muscipula*).

Background of the Invention

As disclosed in European Application No. 19,808 (corresponding to application No. 80 102 707), the juices or extracts of certain carnivorous plants are suitable for the treatment of cancer. Juice extracts from parts of the Venus Fly Trap (*Dionaea muscipula*) have been found to be particularly efficacious. These extracts contain, among other things, specific proteolytic ferments which can be taken orally, or by injection after filtration and dilution with cooking salt solutions.

As disclosed in EHK Acta medica empirica, Bd. 34, 416–420 (1985), therapeutic effects are attributed to specific endonucleases found in the juice extract from carnivorous plants. The endonucleases provide for a partial inhibition of cell division of tumor cells, which in many cases promotes remission, and sometimes disappearance, of the tumor. Even patients with metasthesis symptoms have been successfully treated with a commercial composition designated as CARNIVORA TM, which is marketed by Carnivora, GmbH, Jagsthausen. The Carnivora composition consists of a diluted juice extract or the lyophilized solids of the extracted juice of fresh plant parts of *Dionaea muscipula*. The composition is taken orally, by intramuscular injection after dilution of the lyophilized powder in water, or by inhalation of an aerosol spray after dilution in water.

Herpes is characterized by small blisters which suddenly appear, usually in the transient region between the epidermis and the mucosa, for example in the region of the nose or the lips, or the genitalia or the anus. Herpes can also appear in other regions of the body and can appear as herpes Zoster in connection with a neuralgic rash. Herpes frequently appears as a result of external pressure on the organism, such as disease accompanied by fever, strong facial sunburn or exposure to the sun, etc. The herpes blisters can become sores which cause pain and swelling and which heal with difficulty.

Known herpes treatments, such as those relying on tinctures or zinc ointments, or on oral administration of vitamin B, frequently do not lead to symptomatic relief or the desired cure.

Granulatomous-inflammatory diseases of the ileum and colon, known as regional enteritis or Morbus Crohn, is a frequently encountered condition. Symptoms include chronic diarrhea and abdominal pains. The therapy available for this disease is frequently symptomatic, and is aimed at reducing diarrhea and abdominal pain. Antibacterial medications have been used to treat bacterial complications, but have not achieved a cure. Corticos steroids are useful, but frequently a surgical or operative intervention is needed, such as a resection of the diseased intestinal portion. This is also true of Colitis ulcerosa. In difficult cases, a total proctocolectomy or iletostomy, respectively, is required.

Unexpectedly, it lately has been discovered that the juice or aqueous extract of carnivorous plants is effective for the treatment of herpes infections by oral administration or local application, and for the treatment of chronic inflammations of the intestinal tract (Morbus Crohn and Colitis ulcerosa)—even though these diseases are entirely different from the sarcoma and carcinoma diseases heretofore treated with the known extract, and even though the treatment according to the invention differs from known medications and procedures for the treatment of herpes and Crohn's disease.

Summary of the Invention

According to the invention, herpes, Morbus Crohn and Colitis ulcerosa are treated with a medication prepared from the juice or aqueous extract of meat-eating plants, preferably the Venus Fly Trap (*Dionaea muscipula*).

For herpes, the preparation is applied locally in liquid form, as a compress, poultice, or directly, with or without dilution in water or alcohol. A significant improvement and reduction in inflammation appears within a few days, followed by prompt healing. It appears that, due to the constituents of the juice extract of carnivorous plants, the diseased cell structure of the epidermis is decomposed and resolved, so that a new and healthy epidermis can form. However, even when taken orally, the extract effects a significant improvement, and provides for healing of the diseased skin region over time.

In order to obtain a preparation of longer duration, the juice of carnivorous plants extracted by a juicer can be lyophilized in a conventional fashion. For use, the lyophilized extract is dissolved in water or a thinned cooking salt solution for oral administration in soft or hard conventional gelatin capsules or local application.

For Morbus Crohn and Colitis ulcerosa, the extract may be applied orally, with or without dilution in water or in a cooking salt solution. The extract is obtained by compressing the carnivorous plant, preferably the leaves, for example in a juicer. Watery extracts from other parts of the plant may also be used. The extract can also be applied in the form of an injection, prepared from juice which has been filtered and diluted, lyophilized, and then dissolved in water prior to injection. The entire Venus Fly Trap, and preferably the leaves thereof, has been found to be particularly suitable according to the invention.

The invention is further described with reference to a number of examples. It will be understood by skilled practitioners that these examples are illustrative, and do not serve to limit the scope of the invention or the appended claims.

Example 1

To produce a locally applicable medication for the treatment of herpes simplex, freshly harvested plant parts of *Dionaea muscipula* are juiced in a conventional fashion, and the resulting juice extract is filtered. The extract can be directly applied to the diseased skin region, or can be applied in the form of a compress or poultice impregnated with the extract or with all indications the average dose is 3×50 drops amounting to 2 to 4 ml per day. The extract can be combined with one or more conventional excipients, such as alcohol, in order to stabilize the medication.

Example 2

An oral medication for herpes can be prepared by diluting an extract obtained and filtered according to Example 1 with alcohol-containing water, hydrous alcohol, or a cooking salt solution in a proportion of 1:3. This diluted solution may be administered several times a day in a dosage of about 2 ml (50 drops).

Example 3

To produce a medication for treatment of Morbus Crohn by injection, freshly harvested plant parts of *Dionaea muscipula* are juiced in a conventional fashion, and the resulting juice extract is filtered. The filtrate, about 200 ml, is lyophilized to form about 4.2 g of lyophilized product. For individual injection, the lyophilized product is stored in ampules, each containing 41.5 mg. For injection, the lyophilized product in the ampule is diluted in water and is injected intramuscularly at a dosage corresponding to about 2 ml of extracted juice.

Example 4

An oral medication for treatment of Morbus Crohn can be prepared by diluting an extract obtained and filtered according to Example 3 with alcohol-containing water or a cooking salt solution in a proportion of 1:3. This diluted solution may be administered several times a day in a dosage of about 2 ml (50 drops).

We claim:

1. A method for treating herpes comprising administering to a host afflicted by same juice of the aqueous solution of juice extracted from *Dionaea muscipula*.

2. The method according to claim 1, comprising administering topically the juice of *Dionaea muscipula*.

3. The method according to claim 1, wherein said juice has been filtered and diluted in alcohol or in a saline solution in a proportion of 1:3, and the thus diluted juice is administered orally in an effective amount of 2 to 4 ml per day.

4. The method according to claim 1 wherein, prior to administration said juice is lyophilized and the lyophilized product is diluted in hydrous alcohol or saline solution.

* * * * *